(12) United States Patent
Asayesh (10) Patent No.: US 10,966,882 B2
(45) Date of Patent: Apr. 6, 2021

(54) ABSORBENT ARTICLE AND METHOD FOR MANUFACTURING ABSORBENT ARTICLE

(71) Applicant: Essity Hygiene and Health Aktiebolag, Gothenburg (SE)

(72) Inventor: Yasha Asayesh, Gothenburg (SE)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 0 days.

(21) Appl. No.: 16/762,689

(22) PCT Filed: Dec. 21, 2018

(86) PCT No.: PCT/SE2018/051361
§ 371 (c)(1),
(2) Date: May 8, 2020

(87) PCT Pub. No.: WO2019/125298
PCT Pub. Date: Jun. 27, 2019

(65) Prior Publication Data
US 2020/0375823 A1 Dec. 3, 2020

(30) Foreign Application Priority Data

Dec. 21, 2017 (WO) .................. PCT/SE2017/00052
Dec. 21, 2017 (WO) .................. PCT/SE2017/00055

(51) Int. Cl.
*A61F 13/15* (2006.01)
*A61F 13/532* (2006.01)
(Continued)

(52) U.S. Cl.
CPC .... *A61F 13/5323* (2013.01); *A61F 13/15203* (2013.01); *A61F 13/15739* (2013.01);
(Continued)

(58) Field of Classification Search
CPC ...... A61F 2013/5315; A61F 2013/5349; A61F 2013/53472; A61F 2013/53925;
(Continued)

(56) References Cited

U.S. PATENT DOCUMENTS 5,330,456 A 7/1994 Robinson
5,622,734 A 4/1997 Clark et al.
(Continued)

FOREIGN PATENT DOCUMENTS

CN 101132751 A 2/2008
CN 101340873 A 1/2009
(Continued)

OTHER PUBLICATIONS

Office Action (Decision on Grant) dated Nov. 23, 2020, by the Federal Service for Intellectual Property in Russian Patent Application No. 2020123924/03(041325) and an English Translation of the Office Action. (27 pages).

(Continued)

*Primary Examiner* — Bradley H Philips
(74) *Attorney, Agent, or Firm* — Buchanan Ingersoll & Rooney P.C.

(57) ABSTRACT

An absorbent article including an absorbent core sandwiched between a liquid-permeable topsheet and a liquid-impermeable backsheet, the article defining a front portion, a back portion and a crotch portion, wherein the absorbent core includes an absorbent component enclosed by a core cover including an upper side and a lower side, and a sealing arrangement for joining the upper and lower sides, wherein the sealing arrangement includes two side seams extending along two side edges in a direction of a longitudinal axis of the core, wherein the sealing arrangement further includes at least one transversally oriented connecting sealing, the at least one connecting sealing joining the side seams, wherein (Continued)

the sealing arrangement further includes welding spots, wherein the sum of the area of the welding spots is constant along a direction of a transversal axis of the core.

15 Claims, 5 Drawing Sheets

(51) Int. Cl.
*A61F 13/539* (2006.01)
*A61F 13/49* (2006.01)
*A61F 13/53* (2006.01)

(52) U.S. Cl.
CPC .......... *A61F 13/539* (2013.01); *A61F 13/49* (2013.01); *A61F 2013/15406* (2013.01); *A61F 2013/530007* (2013.01); *A61F 2013/5395* (2013.01); *A61F 2013/530481* (2013.01); *A61F 2013/53991* (2013.01)

(58) Field of Classification Search
CPC .......... A61F 13/15699; A61F 13/15739; A61F 13/539; A61F 13/4963; A61F 13/515
See application file for complete search history.

(56) References Cited

U.S. PATENT DOCUMENTS

| | | | |
|---|---|---|---|
| 6,102,900 A | 8/2000 | Roessler et al. | |
| 6,563,013 B1 | 5/2003 | Murata | |
| 9,132,046 B2 * | 9/2015 | Glaug | A61F 13/4946 |
| 9,974,698 B2 | 5/2018 | Jackels | |
| 10,071,000 B2 * | 9/2018 | Umemoto | A61F 13/51108 |
| 10,149,788 B2 | 12/2018 | Kreuzer et al. | |
| 10,561,546 B2 | 2/2020 | Rosati et al. | |
| 10,806,642 B2 | 10/2020 | Tagomori et al. | |
| 2001/0014797 A1 | 8/2001 | Suzuki et al. | |
| 2003/0060791 A1 | 3/2003 | Drevik | |
| 2004/0127871 A1 | 7/2004 | Odorzynski et al. | |
| 2004/0138633 A1 | 7/2004 | Mishima et al. | |
| 2004/0243078 A1 | 12/2004 | Guidotti et al. | |
| 2006/0229579 A1 | 10/2006 | Wahlstrom et al. | |
| 2006/0276767 A1 | 12/2006 | Ueminami et al. | |
| 2007/0093164 A1 | 4/2007 | Nakaoka | |
| 2007/0142802 A1 | 6/2007 | Suzuki | |
| 2008/0119810 A1 | 5/2008 | Kuroda et al. | |
| 2008/0132864 A1 | 6/2008 | Lawson et al. | |
| 2009/0036854 A1 | 2/2009 | Guidotti et al. | |
| 2009/0082744 A1 | 3/2009 | Hakansson et al. | |
| 2009/0088718 A1 | 4/2009 | Toyoshima et al. | |
| 2009/0270825 A1 | 10/2009 | Wciorka et al. | |
| 2010/0168700 A1 | 7/2010 | Schmidt et al. | |
| 2010/0262099 A1 | 10/2010 | Klofta | |
| 2010/0268183 A1 * | 10/2010 | Een | B29C 65/08 604/385.01 |
| 2011/0004178 A1 | 1/2011 | Fernkvist et al. | |
| 2011/0250413 A1 | 10/2011 | Lu et al. | |
| 2012/0143164 A1 | 6/2012 | Frank et al. | |
| 2012/0296301 A1 | 11/2012 | Lawson et al. | |
| 2012/0312491 A1 | 12/2012 | Jackels et al. | |
| 2012/0316526 A1 | 12/2012 | Rosati et al. | |
| 2012/0316528 A1 * | 12/2012 | Kreuzer | A61F 13/536 604/366 |
| 2012/0316529 A1 | 12/2012 | Kreuzer et al. | |
| 2012/0316530 A1 | 12/2012 | Armstrong-ostle et al. | |
| 2012/0323195 A1 | 12/2012 | Ehrnsperger et al. | |
| 2012/0325408 A1 | 12/2012 | Hundorf et al. | |
| 2013/0138070 A1 | 5/2013 | Drevik | |
| 2013/0231622 A1 | 9/2013 | Dieringer et al. | |
| 2014/0005625 A1 | 1/2014 | Wirtz et al. | |
| 2014/0027066 A1 | 1/2014 | Jackels et al. | |
| 2014/0088535 A1 | 3/2014 | Xu et al. | |
| 2014/0163500 A1 | 6/2014 | Roe et al. | |
| 2014/0163503 A1 | 6/2014 | Arizti et al. | |
| 2014/0163506 A1 | 6/2014 | Roe et al. | |
| 2014/0163511 A1 | 6/2014 | Roe et al. | |
| 2014/0324007 A1 | 10/2014 | Hundorf et al. | |
| 2014/0324008 A1 | 10/2014 | Hundorf et al. | |
| 2014/0371701 A1 | 12/2014 | Bianchi et al. | |
| 2015/0032073 A1 | 1/2015 | Noda et al. | |
| 2015/0038931 A1 | 2/2015 | Kreuzer et al. | |
| 2015/0051568 A1 | 2/2015 | Sakaguchi et al. | |
| 2015/0065975 A1 | 3/2015 | Roe et al. | |
| 2015/0065976 A1 | 3/2015 | Roe et al. | |
| 2015/0080821 A1 | 3/2015 | Peri et al. | |
| 2015/0173968 A1 | 6/2015 | Joseph | |
| 2015/0245954 A1 | 9/2015 | Varga et al. | |
| 2015/0374562 A1 | 12/2015 | Hippe et al. | |
| 2016/0058630 A1 | 3/2016 | Roe et al. | |
| 2016/0058632 A1 | 3/2016 | Lawson et al. | |
| 2016/0081862 A1 | 3/2016 | Mason et al. | |
| 2016/0206482 A1 | 7/2016 | Nishikawa et al. | |
| 2016/0206485 A1 | 7/2016 | Seitz et al. | |
| 2016/0235595 A1 | 8/2016 | Ehrnsperger et al. | |
| 2016/0235604 A1 | 8/2016 | Ehrnsperger et al. | |
| 2016/0270971 A1 | 9/2016 | Raycheck et al. | |
| 2016/0270982 A1 | 9/2016 | Raycheck et al. | |
| 2016/0270986 A1 | 9/2016 | Stiehl et al. | |
| 2016/0270987 A1 | 9/2016 | Stiehl et al. | |
| 2016/0331602 A1 | 11/2016 | Bianchi et al. | |
| 2016/0346136 A1 | 12/2016 | Strasemeier et al. | |
| 2017/0057157 A1 | 3/2017 | Lebowitz | |
| 2017/0079853 A1 | 3/2017 | Willhaus et al. | |
| 2017/0079857 A1 | 3/2017 | Willhaus et al. | |
| 2017/0172810 A1 | 6/2017 | Van De Maele | |
| 2018/0021187 A1 | 1/2018 | Nishikawa et al. | |
| 2018/0049924 A1 | 2/2018 | Van De Maele | |
| 2018/0049925 A1 | 2/2018 | Van De Maele | |
| 2019/0038477 A1 | 2/2019 | Jackels et al. | |
| 2020/0078229 A1 * | 3/2020 | Van Ingelgem | A61F 13/539 |

FOREIGN PATENT DOCUMENTS

| | | |
|---|---|---|
| CN | 102006846 A | 4/2011 |
| CN | 102770592 A | 11/2012 |
| CN | 103596534 A | 2/2014 |
| CN | 103607990 A | 2/2014 |
| CN | 203988675 U | 12/2014 |
| CN | 104837458 A | 8/2015 |
| CN | 204671400 U | 9/2015 |
| CN | 105816277 A | 8/2016 |
| CN | 107249529 A | 10/2017 |
| CN | 107405240 A | 11/2017 |
| DE | 29513199 U1 | 2/1996 |
| DE | 202012013564 U1 | 12/2017 |
| DE | 202012013571 U1 | 12/2017 |
| DE | 202013012614 U1 | 12/2017 |
| DE | 202013012616 U1 | 12/2017 |
| DE | 202013012617 U1 | 12/2017 |
| DE | 202017005496 U1 | 1/2018 |
| DE | 202017005950 U1 | 4/2018 |
| DE | 202017005952 U1 | 4/2018 |
| DE | 202017005956 U1 | 4/2018 |
| EP | 0813850 A2 | 12/1997 |
| EP | 0958801 A1 | 11/1999 |
| EP | 1110528 A2 | 6/2001 |
| EP | 1880700 A1 | 1/2008 |
| EP | 1679055 B1 | 4/2010 |
| EP | 2444046 A1 | 4/2012 |
| EP | 2740449 A1 | 6/2014 |
| EP | 2740450 A1 | 6/2014 |
| EP | 2740452 A1 | 6/2014 |
| EP | 2886092 A1 | 6/2015 |
| EP | 2886093 A1 | 6/2015 |
| EP | 2905000 A1 | 8/2015 |
| EP | 2949299 A1 | 12/2015 |
| EP | 2949300 A1 | 12/2015 |
| EP | 2949301 A1 | 12/2015 |
| EP | 2949302 A1 | 12/2015 |
| EP | 2979671 A1 | 2/2016 |
| EP | 2717823 B1 | 5/2016 |
| EP | 3058915 A1 | 8/2016 |
| EP | 3058918 A1 | 8/2016 |
| EP | 3111903 A1 | 1/2017 |

(56) References Cited

FOREIGN PATENT DOCUMENTS

| | | | |
|---|---|---|---|
| EP | 3167858 A1 | 5/2017 | |
| EP | 3167859 A1 | 5/2017 | |
| EP | 3238676 A1 | 11/2017 | |
| EP | 3338751 A1 | 6/2018 | |
| EP | 3348246 A1 | 7/2018 | |
| EP | 3403626 A1 * | 11/2018 | ........... A61F 13/539 |
| EP | 3403626 A1 | 11/2018 | |
| EP | 3403632 A1 | 11/2018 | |
| EP | 3453368 A1 | 3/2019 | |
| FR | 2604867 A1 | 4/1988 | |
| GB | 2518174 A | 3/2015 | |
| JP | 2008119081 A | 5/2008 | |
| JP | 2011125360 A | 6/2011 | |
| JP | 2013102888 A | 5/2013 | |
| JP | 3201606U U | 11/2015 | |
| JP | 2016112359 A | 6/2016 | |
| JP | 2016112404 A | 6/2016 | |
| RU | 2260414 C2 | 9/2005 | |
| RU | 2379014 C2 | 1/2010 | |
| WO | 0217842 A2 | 3/2002 | |
| WO | 0217843 A2 | 3/2002 | |
| WO | 02056812 A2 | 7/2002 | |
| WO | 2004006818 A1 | 1/2004 | |
| WO | 2005065611 A1 | 7/2005 | |
| WO | 2007046974 A1 | 4/2007 | |
| WO | 2009001711 A1 | 12/2008 | |
| WO | 2009128757 A1 | 10/2009 | |
| WO | 2011105109 A1 | 9/2011 | |
| WO | 2011106663 A1 | 9/2011 | |
| WO | 2012014436 A1 | 2/2012 | |
| WO | 2014004439 A1 | 1/2014 | |
| WO | 2014/093310 A1 | 6/2014 | |
| WO | 2016065000 A1 | 4/2016 | |
| WO | 2016147760 A1 | 9/2016 | |
| WO | 2016189759 A1 | 12/2016 | |
| WO | 2017053035 A1 | 3/2017 | |
| WO | 2017053036 A1 | 3/2017 | |
| WO | 2017189151 A1 | 11/2017 | |
| WO | 2017189152 A1 | 11/2017 | |
| WO | 2018006027 A1 | 1/2018 | |
| WO | 2018210751 A1 | 11/2018 | |
| WO | 2018210752 A1 | 11/2018 | |
| WO | 2018210753 A1 | 11/2018 | |
| WO | 2018210754 A1 | 11/2018 | |
| WO | 2018210756 A1 | 11/2018 | |
| WO | 2018210757 A1 | 11/2018 | |
| WO | 2018210758 A1 | 11/2018 | |
| WO | 2019005666 A1 | 1/2019 | |
| WO | 2019048397 A1 | 3/2019 | |
| WO | 2019125227 A1 | 6/2019 | |
| WO | 2019125228 A1 | 6/2019 | |

OTHER PUBLICATIONS

Office Action (Notification of the First Office Action) dated Oct. 19, 2020, by the China National Intellectual Property Administration (CNIPA) of the People's Republic of China in corresponding Chinese Patent Application No. 201780096125.0, and an English Translation of the Office Action. (14 pages).
Office Action (Notice of acceptance for patent application) dated Nov. 9, 2020 by the Australian Government—IP Australia in corresponding Australian Patent Application No. 2017443955. (3 pages).
Office Action (Decision on Grant) dated Sep. 28, 2020, by the Federal Service for Intellectual Property in Russian Patent Application No. 2020123912/03(041313) and an English Translation of the Office Action. (25 pages).
Office Action (Notification of the First Office Action) dated Nov. 13, 2020, by the China National Intellectual Property Administration (CNIPA) of the People's Republic of China in corresponding Chinese Patent Application No. 201780096151.3, and an English Translation of the Office Action. (9 pages).
Office Action (Notification of the First Office Action) dated Oct. 20, 2020, by the China National Intellectual Property Administration (CNIPA) of the People's Republic of China in corresponding Chinese Patent Application No. 201780096152.8, and an English Translation of the Office Action. (20 pages).
International Search Report (PCT/ISA/210) and Written Opinion (PCT/ISA/237) dated Mar. 1, 2019, by the Swedish Patent Office as the International Searching Authority for International Application No. PCT/SE2018/051361.
International Search Report (PCT/ISA/210) and Written Opinion (PCT/ISA/237) dated Oct. 10, 2018, by the Swedish Patent Office as the International Searching Authority for International Application No. PCT/SE2018/050383.
International Search Report (PCT/ISA/210) dated Oct. 10, 2018, by the Swedish Patent Office as the International Searching Authority for International Application No. PCT/SE2017/000053.
International Search Report (PCT/ISA/210) dated Oct. 10, 2018, by the Swedish Office as the International Searching Authority for International Application No. PCT/SE2017/000055.
International Search Report (PCT/ISA/210) dated Sep. 3, 2018, by the Swedish Patent Office as the International Searching Authority for International Application No. PCT/SE2017/000050.
International Search Report (PCT/ISA/210) dated Sep. 3, 2018, by the Swedish Patent Office as the International Searching Authority for International Application No. PCT/SE2017/000051.
International Search Report (PCT/ISA/210) dated Sep. 3, 2018, by the Swedish Patent Office as the International Searching Authority for International Application No. PCT/SE2017/000054.
International Search Report (PCT/ISA/210) dated Sep. 7, 2018, by the Swedish Patent Office as the International Searching Authority for International Application No. PCT/SE2017/000052.
Third Party Observation mailed Apr. 7, 2020, in corresponding International Patent Application No. PCT/SE2017/000050, 3 pages.
Third Party Observation mailed on Apr. 2, 2020, by the Swedish Patent Office for International Application No. PCT/SE2017/000051.
Written Opinion (PCT/ISA/237) dated Oct. 10, 2018, by the Swedish Patent Office as the International Searching Authority for International Application No. PCT/SE2017/000053.
Written Opinion (PCT/ISA/237) dated on Oct. 10, 2018, by the Swedish Patent Office as the International Searching Authority for International Application No. PCT/SE2017/000055.
Written Opinion (PCT/ISA/237) dated on Sep. 3, 2018, by the Swedish Patent Office as the International Searching Authority for International Application No. PCT/SE2017/000050.
Written Opinion (PCT/ISA/237) dated on Sep. 3, 2018, by the Swedish Patent Office as the International Searching Authority for International Application No. PCT/SE2017/000051.
Written Opinion (PCT/ISA/237) dated Sep. 3, 2018, by the Swedish Patent Office as the International Searching Authority for International Application No. PCT/SE2017/000054.
Written Opinion (PCT/ISA/237) dated Sep. 7, 2018, by the Swedish Patent Office as the International Searching Authority for International Application No. PCT/SE2017/000052.
Office Action dated Dec. 30, 2020, by the Federal Service for Intellectual Property in Russian Patent Application No. 2020123962103 and an English Translation of the Office Action. (12 pp.).
Office Action (Notification of the First Office Action) dated Dec. 8, 2020 by the China National Intellectual Property Administration (CNIPA) of the People's Republic of China in corresponding Chinese Patent Application No. 201880079974.X, and an English Translation of the Office Action. (18 pp.).

* cited by examiner

ABSORBENT ARTICLE AND METHOD FOR MANUFACTURING ABSORBENT ARTICLE

TECHNICAL FIELD

The disclosure relates to an absorbent article comprising an absorbent core sandwiched between a liquid-permeable topsheet and a liquid-impermeable backsheet. The disclosure also relates to a method for manufacturing an absorbent article of the above-mentioned type.

BACKGROUND

Wearable and disposable absorbent articles, for example in the form of diapers, incontinence garments, feminine garments and the like, are well known. Such articles are used to absorb, distribute and store various types of body exudates while providing a high level of comfort and sense of dryness to the wearer during use.

A conventional disposable absorbent article in the form of a diaper is normally designed with an absorbent core which is sandwiched between a topsheet and a backsheet. The article is arranged along a longitudinal axis and along a transversal axis which extends in a perpendicular direction in relation to the longitudinal axis. Furthermore, the article can be divided into a front portion, a back portion and a crotch portion.

The absorbent article will absorb body exudates when it is worn. A potential disadvantage which may occur when the absorbent article is in its wet condition is that the crotch portion may sag and hang down. This tendency for sagging is unwanted and may lead to insufficient comfort, fit and function of the article.

A previously known absorbent article of the above-mentioned kind is disclosed in the patent document US 2012/316528. This document shows a disposable diaper having an absorbent core which, according to an embodiment, comprises longitudinally extending channels. The purpose of the diaper is to provide good liquid handling properties and an increased flexibility and improved fit during use.

Even though the article disclosed in US 2012/316528 fulfills certain requirements related to liquid handling and fit, there is still a need for further improvements.

SUMMARY

The present disclosure is based on the insight that the ability of an absorbent article such as for example a diaper, to avoid sagging in its wet condition during use, may be influenced by certain features of the article.

There is provided an absorbent article comprising an absorbent core sandwiched between a liquid-permeable topsheet and a liquid-impermeable backsheet, said article being arranged along a longitudinal axis and a transversal axis extending in a perpendicular direction in relation to the longitudinal axis and said article defining a front portion, a back portion and a crotch portion, wherein said absorbent core comprises an absorbent component enclosed by a core cover comprising an upper side and a lower side, and a sealing arrangement for joining said upper and lower sides, wherein said sealing arrangement comprises two side seams extending along two side edges in the direction of the longitudinal axis of said core, wherein said sealing arrangement further comprises at least one transversally oriented connecting sealing, said at least one connecting sealing joining said side seams, wherein said sealing arrangement further comprises welding spots, wherein the sum of the area of the welding spots is constant along the direction of the transversal axis.

Further, the sealing arrangement may comprise two channel sealings extending along the longitudinal axis in the crotch portion.

The absorbent component may, in embodiments, not extend beyond the at least one connecting sealing and the side seams.

The absorbent article may comprise a first connecting sealing and a second connecting sealing, wherein said first connecting sealing joins said side seams at the front portion and wherein said second connecting sealing joins said side seams at the back portion of the absorbent core.

The sum of the amount of welding spots along the direction of the transversal axis may be constant.

The at least one connecting sealing may be symmetrically aligned with respect to the longitudinal axis.

Further, the angle between the longitudinal axis and the first connecting sealing may be less than 90 degrees, and wherein the angle between the longitudinal axis and the second connecting sealing may be more than 90 degrees.

The distance between the welding spots in transversal direction in the first connecting sealing may differ from the distance between the welding spots in the second connecting sealing.

The sealing arrangement may generally follow the outline of the absorbent component in at least one part of the sealing arrangement.

At least one of the connecting sealings may generally follow the outline of the absorbent component, wherein at least one of the connecting sealings may deviate from the outline of the absorbent component.

The maximum length in the longitudinal direction of the first connecting sealing may differ from the maximum length in the longitudinal direction of the second connecting sealing.

The maximum length in the longitudinal direction of the first connecting sealing may be greater than the maximum length in the longitudinal direction of the second connecting sealing.

The at least one connecting sealing may be V-shaped. The first connecting sealing may be V-shaped pointing towards the central transversal axis and the second connecting sealing may be V-shaped also pointing towards the central transversal axis.

Further the welding spots may be circular, rectangular, oblong or oval shaped.

Furthermore, the sum of the amount of welding spots along the transversal direction is between the range of 2-20, and may be within the range of 4-8. The connecting sealing may be sealed by a thermo and/or mechanical welding process such as ultrasonic welding.

There is also provided a method for manufacturing an absorbent article comprising a longitudinal axis and a transversal axis extending in a perpendicular direction in relation to the longitudinal axis and said article comprising a front portion a back portion and a crotch portion, said method comprising:

forming an absorbent core with an absorbent component and enclosing said absorbent component in a core cover comprising an upper side and a lower side;

providing two side seams and at least one connecting sealing joining said upper and lower core cover sides;

sandwiching said absorbent core between a liquid-permeable topsheet and a liquid-impermeable backsheet, wherein said method further comprises: forming said two side seams and said at least one connecting sealing by a thermo and/or mechanical welding process comprising a plurality of welding spots being welded along the direction of the longitudinal axis, wherein the sum of the area of the welding spots is constant along the direction of the transversal axis.

Further advantages and advantageous features of the disclosure are disclosed in the following description.

BRIEF DESCRIPTION OF THE DRAWINGS

The disclosure will be described in greater detail below with reference to the figures shown in the appended drawings.

DETAILED DESCRIPTION

Different aspects of the present disclosure will be described more fully hereinafter with reference to the enclosed drawings. The embodiments disclosed herein can, however, be realized in many different forms and should not be construed as being limited to the aspects set forth herein.

Figure 1:
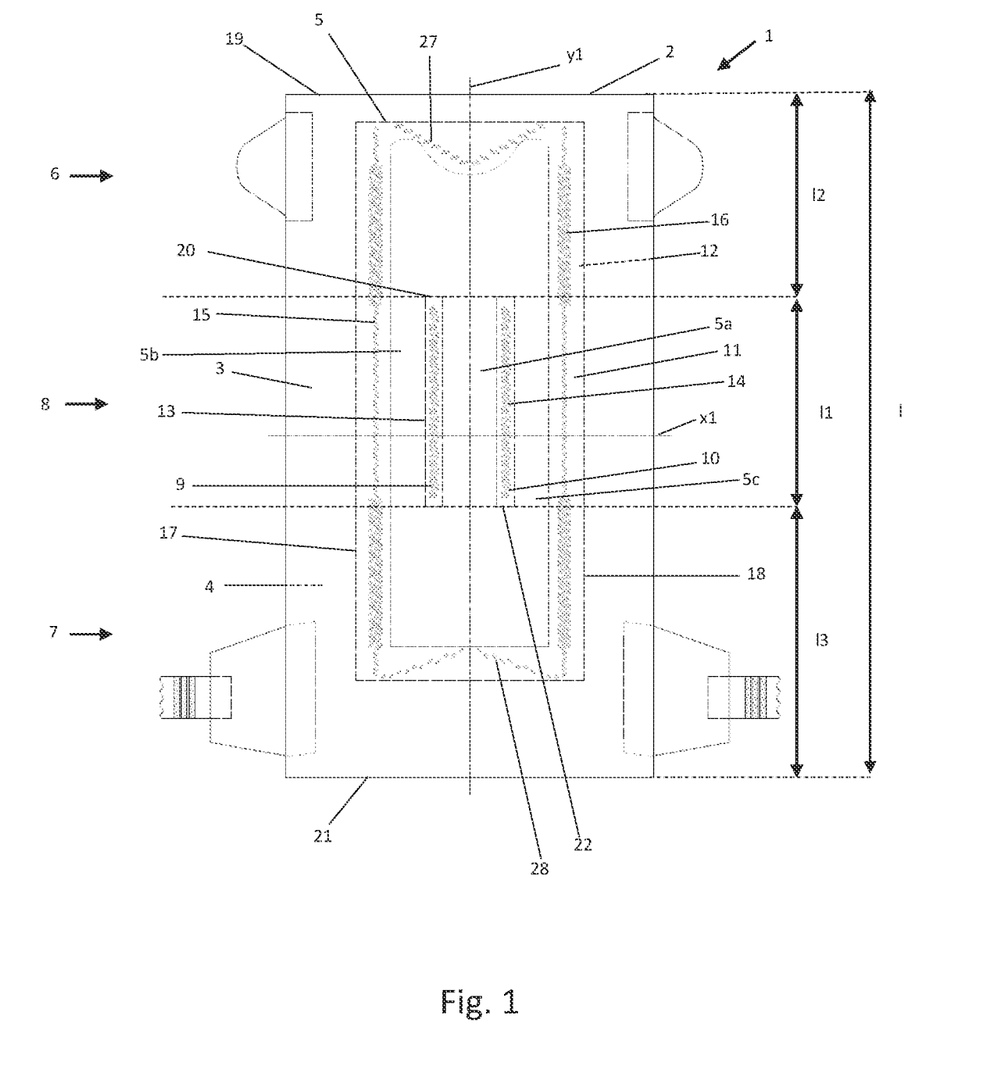
FIG. 1 shows a view from above of an absorbent article in the form of a diaper.

With initial reference to FIG. 1, there is shown a view from above of an absorbent article 1 in the form of a baby diaper. The absorbent article 1 is shown in FIG. 1 in an unfolded and flat state. Also, the absorbent article 1 is based on an absorbent structure for absorbing body exudates from a wearer to provide a dry and comfortable fit for the wearer.

As shown in FIG. 1, the absorbent article 1 comprises a liquid-permeable topsheet 3, a liquid-impermeable backsheet 4 an absorbent core 5 which is sandwiched between the topsheet 3 and the backsheet 4. The topsheet 3 is arranged at the surface of the article 1, i.e., at the side which is facing the wearer, whereas the backsheet 4 is arranged at the underside of the article 1. Furthermore, both the topsheet 3 and the backsheet 4 extend laterally outside of the absorbent core 5 along the entire perimeter of the article 1.

The absorbent core 5 shown in FIG. 1 has a generally rectangular design. However, the disclosure is not limited to this design but can be formed in generally any geometric form within the scope of the disclosure.

The topsheet 3, backsheet 4 and the absorbent core 5 may consist of any materials suitable for their purpose, as will be discussed in further detail below.

As shown in FIG. 1, the absorbent article 1 has a longitudinal extension along a longitudinal axis y1 and a transverse extension along a transverse axis x1, which is perpendicular to the longitudinal axis y1. Furthermore, the absorbent article 1 can be defined as being divided into a front portion 6, a back portion 7 and a crotch portion 8. The front 6 and back portions 7 each having a waist edge 2. The front portion 6 is intended to be oriented in a direction towards the wearer's belly during use of the article 1.

Figure 2:
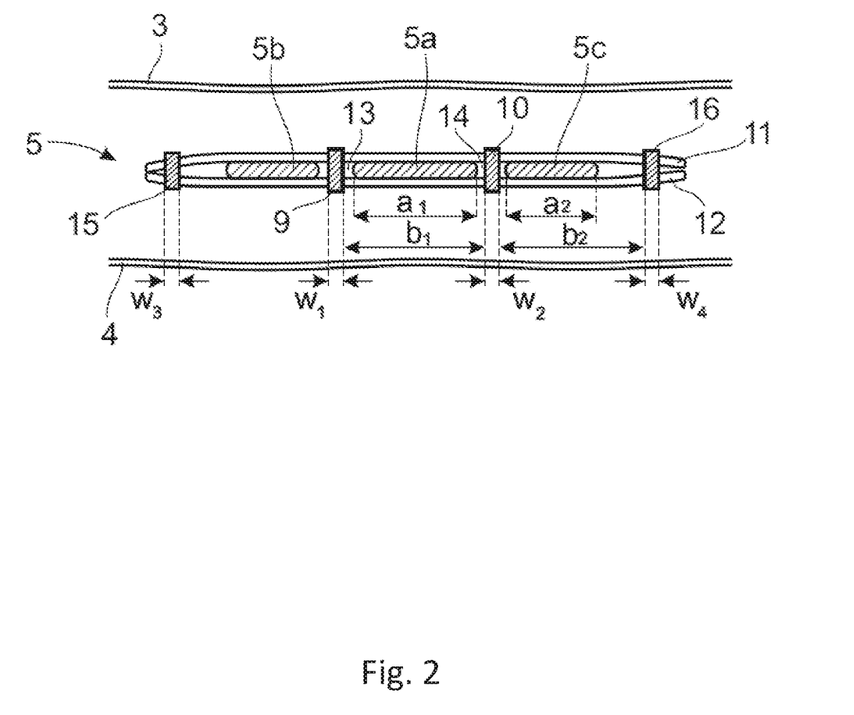
FIG. 2 shows a cross-sectional view of the diaper.

Furthermore, with reference to FIGS. 1 and 2, wherein FIG. 2 is a cross-sectional view of the absorbent article 1 along the transversal axis x1, it should be noted that the absorbent core 5 comprises an absorbent component 5a, 5b, 5c which is enclosed by a core cover comprising an upper side 11 and a lower side 12, and is formed with two longitudinally extending and generally straight channel sealings 9, 10 which are configured so as to join the upper side 11 to the lower side 12, see in particular FIG. 2, wherein the absorbent component 5a, 5b, 5c is sandwiched between said upper side 11 and said lower side 12.

According to FIGS. 1 and 2, the core cover is formed by a separate upper core cover layer and a separate lower core cover layer. However, the disclosure is not limited to a core cover comprising two separate material layers. The core cover may also be of one single material layer. The absorbent component 5a, 5b, 5c may be enclosed by one core cover layer folded in two, or enclosed by a continuous core cover sheet, thereby providing upper and lower core cover sides for wrapping the absorbent component.

The upper side 11 and the lower side 12 is attached to each other by thermo and/or mechanical bonding, such as thermosealing or ultrasonic welding. The attachment may also comprise adhesive bonding, stitching or the like, or combinations of the same. According to the embodiment shown in FIGS. 1 and 2, the upper side 11 and the lower side 12 are attached to each other by ultrasonic welding.

The channel sealings 9, 10 are positioned along two corresponding channels 13, 14 which constitute sections of the absorbent core 5 which are not filled with absorbent material. This is obtained through manufacturing the absorbent core 5 involving a mat forming process during which absorbent material is omitted from the areas which correspond to the channels 13, 14. In this manner, no absorbent material will be present in the channels 13, 14, i.e., where the channel sealings 9, 10 are arranged.

As shown in FIGS. 1 and 2, the absorbent core 5 may be divided into a centre segment 5a and two side segments 5b, 5c in at least the crotch portion 8. The two above-mentioned channels 13, 14, and the channel sealings 9, 10 will consequently be configured so that they separate the three segments 5a, 5b, 5c from each other along the crotch area 8. Also, the length l1 of each channel sealing 9, 10 may correspond to the length of the crotch portion 8 and may also be slightly less than the length of each channel 13, 14.

The absorbent core 5 may be generally rectangular and comprise two generally straight channel sealings 9, 10 which are generally parallel to said longitudinal axis y1 and define a first channel sealing width w1 and a second channel sealing width w2. The disclosure is not limited to a rectangular core 5 and generally straight channel sealings 9, 10, i.e., other geometrical configurations may occur. The channel sealings 9, 10 are positioned within the first channel 13 and the second channel 14, respectively, and are configured to attach the upper side 11 to the lower side 12.

Furthermore, the centre segment 5a is defined in the core 5 between the channel sealings 9, 10. Also, the two side segments 5b, 5c are defined in the core 5 outside each channel sealing 9, 10. More precisely, the first side segment 5b is positioned between the first channel sealing 9 and a first side seam 15, whereas the second side segment 5c is positioned between the second channel sealing 10 and a second side seam 16. The side seams 15, 16 are configured for joining the upper core cover side 11 to the lower side 12, suitably by means of ultrasonic welding or other relevant technologies as described above with reference to the channel sealings 9, 10. Furthermore, the side seams 15, 16 extend along each side of the absorbent core 5, along a first side edge 17 and a second side edge 18 of the absorbent core 5.

The absorbent core 5 may comprise at least one connecting sealing 27, 28 that joins the side seams 15, 16, the at least one connecting sealing 27, 28 may be transversally oriented crossing the longitudinal axis y1. As shown in FIG. 1, the absorbent core 5 may comprise a first connecting sealing 27 and a second connecting sealing 28. The first and second connecting sealings 27, 28 may be situated at the front portion 6 and the back portion 7 of the absorbent article 1 respectively. The number of connecting sealings 27, 28 is not limited to two, it could be less than two connecting sealings 27, 28 and more than two connecting sealings 27, 28. Further, the connecting sealings 27, 28 could also be situated in the crotch portion 8. The connecting sealings 27, 28 are constructed to join the side seams 15, 16.

By having the connecting sealings 27, 28 situated as disclosed in FIG. 1, i.e., one connecting sealing 27 joining the end of the side seams 15, 16 situated at the front portion 6 of the absorbent article 1 and one connecting sealing 28 joining the end of the side seams 15, 16 situated at the back portion of the absorbent article 1, this allows the side seams 15, 16 and the connecting sealings 27, 28 to form a closed structure. The mentioned structure could also be called a sealing arrangement 15, 16, 27, 28. The sealing arrangement 15, 16, 27, 28 could be defined as a means for joining upper and lower core cover sides by welding spots 23. The absorbent component 5a, 5b, 5c may be enclosed by this closed structure. In other words, it may be constructed such that the absorbent component 5a, 5b, 5c does not extend beyond the side seams 15, 16 and the at least one connecting sealing 27, 28. The closed structure form may allow for improved joining of the upper and lower core cover 11, 12 sides, achieving a more rigid closure. Further, the closed structure form enables the swellable components within the absorbent core 5 to stay within the closed structure form to a greater extent compared to an open structure form, this may lead to a better fit and improved closure of the absorbent article 1. Having a connecting sealing 27 in at least the front portion of the absorbent article may allow for less pressure towards the navel of the user of the absorbent article.

The connecting sealings 27, 28 may generally follow the outline of the absorbent component in at least one part of the sealing arrangement 15, 16, 27, 28. At least one of the connecting sealings 27, 28 may deviate from the outline of the absorbent component. As disclosed in FIG. 1 the first connecting sealing 27 may generally follow the outline of the absorbent component in the front portion 6, and the second connecting sealing 28 may deviate from the outline of the absorbent component at the back portion 7. Further, the side seams 15, 16 may follow the outline of the absorbent component. In FIG. 1 the first connecting sealing 27 is arrow-shaped following the outline of the absorbent component 5a, 5b, 5c. Further, at the back portion 7 the second connecting sealing 28 is also arrow-shaped, but the absorbent component 5a, 5b, 5c has an outline being a straight transversal line that, in other words, deviates from the shape of the connecting sealing 28.

The absorbent article 1 may have a single connecting sealing 27, 28 located at either the front portion 6 or the back portion 7, such a construction of the connecting sealings 27, 28 could be beneficial in a product where the aim is to improve the rigidness of the absorbent article 1 in one single portion of the article. In other words, the sealing arrangement 15, 16, 27, 28 could also be disclosed to not fully enclose the absorbent component 5a, 5b, 5c. Further, the sealing arrangement 15, 16, 27, 28 may also comprise channel sealings 9, 10.

The length 11 of the crotch portion 8 may be equal to the length of the channel sealings 9, 10, i.e., the channel sealings 9, 10 may extend along the crotch portion 8 only. However, the side seams 15, 16 may not just be positioned along the crotch portion 8 but also extend along the front portion 6 and the back portion 7. This will be described in detail below. The absorbent core 5 may be formed with a sealing arrangement which may be constituted by two channel sealings 9, 10, two side seams 15, 16 and at least one connecting sealing 27, 28. The sealing arrangement 15, 16, 27, 28 is configured so that the absorbent core 5 is divided into a centre segment 5a and two side segments 5b, 5c. More precisely, and as shown in FIG. 2, the centre segment 5a has a first width a1 and each side segment 5b, 5c has a second width a2. Also, a third width b1 is defined between the two channel sealings 9, 10. Furthermore, a fourth width b2 is defined between the first channel sealing 9 and the first side seam 15, and between the second channel sealing 10 and the second side seam 16.

According to FIGS. 1 and 2, the absorbent component 5a, 5b 5c is configured so that the weight of absorbent material of the centre segment 5a is generally equal to or greater than the weight of absorbent material in each one of the side segments 5b, 5c. As will be described in greater detail below, the absorbent material may comprise a mixture of pulp material and superabsorbent material. Also, the ratio of the first width a1 and the third width b1 is greater than the ratio of the second width a2 and the fourth width b2. In practical terms, this means that the available space for the absorbent material to expand in the centre segment 5a, during use of the absorbent article 1, is less than the corresponding available space for each side segment 5b, 5c. This will lead to a situation in which the centre segment 5a will be stiffer (in its wet condition) than the side segments 5b, 5c. This means that any tendency in the crotch portion 8 of the absorbent article 1 to sag will be reduced.

The expression "generally equal" as used above for describing the weight of absorbent material in the centre segment 5a as compared with the side segments 5b, 5c should be interpreted in a manner wherein the weight of absorbent material could have a variation of approximately ±5 weight % in any part of the crotch portion 8.

The absorbent component 5a,5b,5c in the crotch portion may be configured so that 33-41 weight % of the absorbent material is in the centre segment 5a, whereas 25-33 weight % of the absorbent material is in each one of the side segments 5b, 5c. In this manner, the desired stiffness in the centre segment 5a may be obtained.

In summary, the absorbent core 5 comprises an absorbent component which in turn comprises the three above-mentioned segments 5a, 5b, 5c of the absorbent article 1. The absorbent component 5a, 5b, 5c comprises absorbent material which may be in the form of pulp material and superabsorbent material. The pulp material may have a basis weight which is in the interval of 50-400 g/m$^2$ and the superabsorbent material may have a basis weight which is in the interval of 100-900 g/m$^2$. However, a deviation of ±5% of the chosen basis weight is accepted.

Various types of materials may be used for the absorbent article 1. The topsheet 3 is arranged to face the wearer of the absorbent article 1 when worn. The topsheet 3 may be formed by a fluid permeable nonwoven fabric or film which is made of thermoplastic synthetic fibers. The topsheet 3 may be sufficiently liquid-permeable to allow discharged body fluids to penetrate through the thickness of the topsheet 3. Also, the topsheet 3 may be suitably manufactured from a material which is compliant and soft-feeling to the skin of the wearer. The topsheet 3 may consist of a single layer or have a laminate structure comprising a plurality of layers, for example, two or more layers. The layers may be made of the same material, or some, or all the layers, may be made of different materials.

The layer of the topsheet 3 or, for the case of a laminate structure, one, some or all the layers of the topsheet may be made of a single material or have plural portions made of different materials, e.g., within different parts of the wearer-facing surface of the topsheet.

The layer of the topsheet 3 or, for the case of a laminate structure, one, some or all of the layers of the topsheet may be a nonwoven material, a perforated plastic film, a plastic or textile mesh, or a liquid permeable foam layer.

The layer of the topsheet 3 or, for the case of a laminate structure, one, some or all of the layers of the topsheet may be, for example, a hydrophilic, non-apertured nonwoven web of fibers, such as natural fibers, e.g., cotton or pulp fibers, synthetic fibers, e.g., polyester or polypropylene fibers, or a combination of these fibers.

The topsheet may have a basis weight in the range of 8-40 g/m$^2$. However, the disclosure is not limited to topsheets having this basis weight only.

Furthermore, the backsheet 4 may be constituted by a liquid-impermeable and breathable layer such as a polymeric film, for example a film of polyethylene or polypropylene.

According to different embodiments, the materials which may be used for the backsheet 4 include thin and flexible fluid impermeable plastic films, or fluid impermeable nonwoven materials, fluid impermeable foams and fluid impermeable laminates.

The backsheet 4 may be formed by a single layer, but may alternatively be formed by a multi-layered structure, i.e., a laminate, wherein at least one layer is fluid impermeable. Furthermore, the backsheet 4 may be elastic in any direction.

Furthermore, the backsheet 4 may have a laminate structure comprising a liquid barrier sheet and a nonwoven layer arranged on top of each other (not shown in detail in the drawings), wherein the nonwoven layer is arranged at an outer side away from the wearer of the absorbent article 1 when worn. The nonwoven layer may be made of thermoplastic polymer material fibers or filaments. The nonwoven layer may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials. The nonwoven layer may have a basis weight in the range of 5-40 g/m$^2$.

The liquid barrier sheet may be made of a plastic material, for example a thermoplastic film material, and/or a nonwoven material. For example, the liquid barrier sheet may be formed as a plastic layer, e.g., a thermoplastic layer, or a plastic film, e.g., a thermoplastic film. Forming the liquid barrier sheet of a plastic material, such as a thermoplastic film material, allows for a particularly good printability of the liquid barrier sheet. The liquid barrier sheet may also contain paper fibers. The liquid barrier sheet may be a liquid impermeable, breathable or non-breathable layer. The liquid barrier sheet may consist of a single layer or have a laminate structure with a plurality of layers, e.g., two or more layers, three or more layers, or four or more layers. The layers of the liquid barrier sheet may be laminated, bonded or attached to each other, for example, by thermo-mechanical bonding, such as thermo-sealing, ultrasonic bonding, such as ultrasonic welding, an adhesive or adhesives, stitching or the like. The liquid barrier sheet may be a breathable microporous film. The microporous film may be made of a material comprising at least two basic components, namely a thermoplastic elastomeric polyolefin polymer and a filler. These components and, in some embodiments, additional other components can be mixed together, heated and subsequently extruded into a mono-layer or multi-layer film using any one of various film-producing processes, such as cast embossed, chill and flat cast, and blown film processes.

Regarding the choice of materials for the various layers in the absorbent article, the materials may be chosen for the bonding process to form the connecting sealings 27, 28, channel sealings 9, 10 and side seams 15, 16. For example, if ultrasonic welding is chosen for joining the upper and lower core cover sides 11, 12, the chosen materials for the core cover may be adapted to form a secure bond during ultrasonic welding.

Furthermore, the absorbent core 5 is provided between the topsheet 3 and the backsheet 4 to absorb the liquid, such as urine or other bodily fluids, which has passed through the topsheet 3. The absorbent core 5 may be made of one layer only, or of two or more layers. The absorbent core 5 may comprise suitable amounts of superabsorbent particles. Such superabsorbent material is well known in the field of absorbent articles, and is constituted by a water-swellable and water-insoluble material which is capable of absorbing large quantities of fluid upon formation of a hydrogel. The absorbent core 5 may contain superabsorbent material in the form of fibers or particles of absorbent polymer material. For example, the superabsorbent material may be surface cross-linked, partially neutralized polyacrylates.

The superabsorbent material, e.g., the superabsorbent fibers or particles, may be mixed with other absorbent or liquid uptake material or materials, such as cellulose fluff pulp, and/or arranged in pockets or layers in the absorbent core 5. The ratio of superabsorbent material and pulp in the absorbent core 5 may be 0-50 weight % pulp fibers and 50-100 weight % superabsorbent material, or 0-30 weight % pulp fibers and 70-100 weight % superabsorbent material.

The absorbent core 5 may further comprise components for improving the properties of the absorbent core 5. For example, the absorbent core 5 may comprise a binder or binders, such as binder fibers.

The core cover 11,12 may be formed by a separate upper core cover 11 layer and a separate lower core 12 cover. However, the disclosure is not limited to a core cover 11,12 comprising two separate core cover layers. The core cover 11,12 may also be of one single material layer. The absorbent component may be enclosed by one core cover layer folded in two, or enclosed by a continuous core cover sheet, thereby providing upper and lower core cover sides for wrapping the absorbent component. The core cover 11,12 may be made of thermoplastic polymer material fibers or filaments. The core cover 11,12 may be made of nonwoven material. The nonwoven layer may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials. The core cover may be configured with a basis weight which is in the interval 5-20 g/m$^2$.

Furthermore, as known by the skilled person, the various layers of the absorbent article 1 may be attached by means of adhesive material. Such adhesive is not shown in the drawings.

One or more additional layers may be provided in the absorbent article 1. For example, an acquisition layer may be arranged between the absorbent core 4 and the topsheet 3. Such an additional layer may for example be in the form of an airlaid layer, a spunlace layer, a high-loft, foam or any other type of material layer which may be used in an absorbent article to act as a liquid acquisition and absorption layer. The acquisition layer is adapted to quickly receive and temporarily store discharged liquid before it is absorbed by the absorbent core. Such acquisition layer may be composed of for example airlaid nonwoven, spunlace nonwoven, high loft nonwoven or foam materials. An airlaid nonwoven may be produced with fluff, wood pulp, and here the fluff fibres are dispersed into a fast-moving air stream and condensed onto a moving screen by means of pressure and vacuum.

According to an embodiment, the ratio of the first width a1 of the centre segment 5a and the third width b1, i.e., the distance between the channel sealings 9, 10 (i.e., a1/b1) is in the interval 0.75-0.91, such as 0.80-0.86. Furthermore, the ratio of the second width a2 of each side segment 5b, 5c and the fourth width b2, i.e., the distance between each channel sealing 9, 10 and its corresponding, adjacent side seam 11, 12 (i.e., a2/b2) is in the interval 0.57-0.71, such as 0.62-0.66. In this manner, the required stiffness of the centre segment 5a may be obtained.

In general, the article 1 is arranged so that the ratio of the first width a1 and the third width b1 is greater than the ratio of the second width a2 and the fourth width b2, i.e.

$$(a1/b1) > (a2/b2)$$

Furthermore, the first, second, third and fourth widths a1, a2, b1, b2, respectively, may be configured so that:

$$b1 < b2*2 \text{ and } a1 < a2*2$$

In addition to the arrangement of the first, second, third and fourth widths a1, a2, b1, b2, as described above, the absorbent article 1 is arranged to provide the desired stiffness of the centre segment 5a and the entire absorbent article 1 by the above-mentioned arrangement of the absorbent material in the absorbent core 5. This means that the centre segment 5a is configured for a stiffness in a wet condition which is greater than that of each side segment 5b, 5c. This also means that the absorbent component, i.e., consisting of the centre segment 5a and the side segments 5b, 5c, may be configured with an ability to expand on wetting and to display a first volume in dry condition and a second volume in completely expanded wet condition, the second volume being greater than the first volume.

With reference again to FIG. 1, it can be noted that each channel sealing 9, 10 may have a length 11 which corresponds to the longitudinal extension of the crotch portion 8. Each one of the channel sealings 9, 10 may have a length 11 which is between 5-50%, such as 10-50%, such as between 28-38%, of the total length l of the absorbent article 1. Furthermore, each channel sealing 9, 10 may have a length 11 which is 10-60%, 20-60% or 30-50%, of the length of the absorbent core 5.

A further parameter is the positioning of the channel sealings 9, 10 along the absorbent article 1 in its longitudinal direction. Such positioning may be defined by choosing a suitable value for the distance 12 between the front edge 19 of the article 1 and the front edge 20 of each channel sealing 9, 10. This means that decreasing said distance 12 means that the distance 13 between the back edge 21 of the article 1 and the back edge 22 of the channel sealings 9, 10 will be increased, and vice versa.

The position of the channel sealings 9, 10 along the longitudinal direction of the absorbent article 1 may be chosen in a manner so that the distance 12 between the front edge 17 of the article 1 and the front edge 18 of each channel 9, 10 is 15-40% or 22-25%, of the total length l of the article 1.

As mentioned above, the absorbent component 5a, 5b, 5c is enclosed by a core cover comprising an upper side 11 and a lower side 12. The absorbent core 5 may be manufactured as a single layer which is wrapped in nonwoven material and positioned between the topsheet 3 and the backsheet 4 during manufacturing of the absorbent article 1.

Furthermore, the topsheet 3 may comprise at least one additive material such as a skin care composition, at least the surface above the side segments 5b, 5c. This is due to that the side segments 5b, 5c normally will be closest to the body of the wearer of the absorbent article 1. The additive may be located on the parts of the topsheet covering the side segments 5b, 5c.

According to what is known to the skilled person, the absorbent article 1 may additionally be provided with further components such as fastening tabs, elastic elements and other components which are commonly used in absorbent articles such as for example baby diapers or incontinence garments. Such additional components are not described in detail here.

With reference to FIG. 1, an absorbent core 5 is provided with a sealing arrangement 9, 10, 15, 16, 27, 28, i.e., comprising the above-mentioned channel sealings 9, 10, the side seams 15, 16 and the connecting sealings 27, 28. As shown in FIG. 1, the side seams 15, 16 extend along the side edges 17, 18 of the core and the connecting sealings 27, 28 joins the side seams 15, 16.

The side seams 15,16 may define a first side seam width w3 and a second side seam width w4, respectively, along the absorbent article 1.

Figure 3:
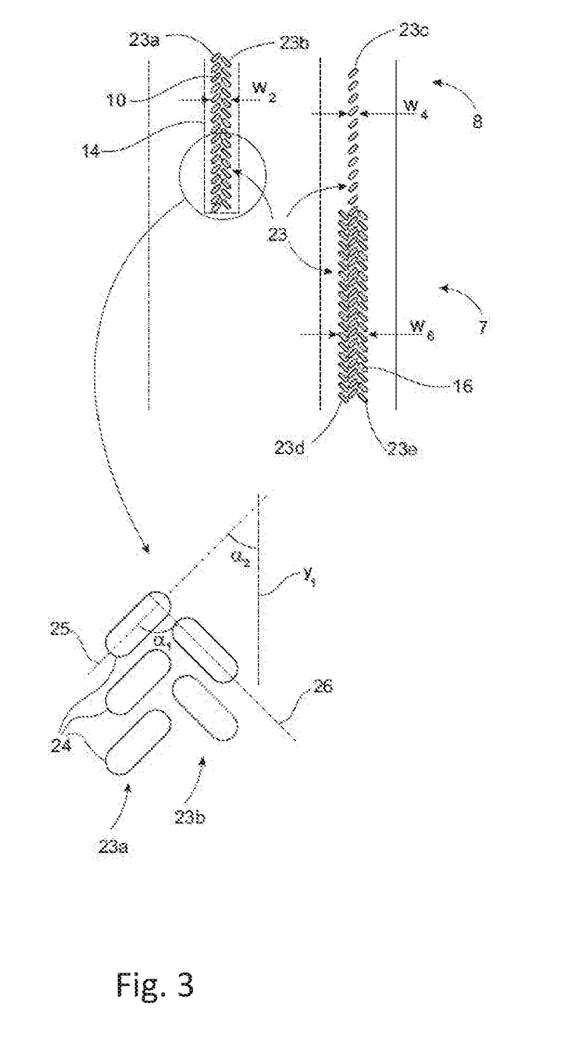
FIG. 3 shows a partial view of a welding pattern and welding spots.

As shown in FIGS. 1 and 3, the channel sealings 9, 10 may be generally straight and generally parallel to the longitudinal axis y1. Also, the side seams 15, 16 may be generally straight and generally parallel to the longitudinal axis y1.

Figure 4:
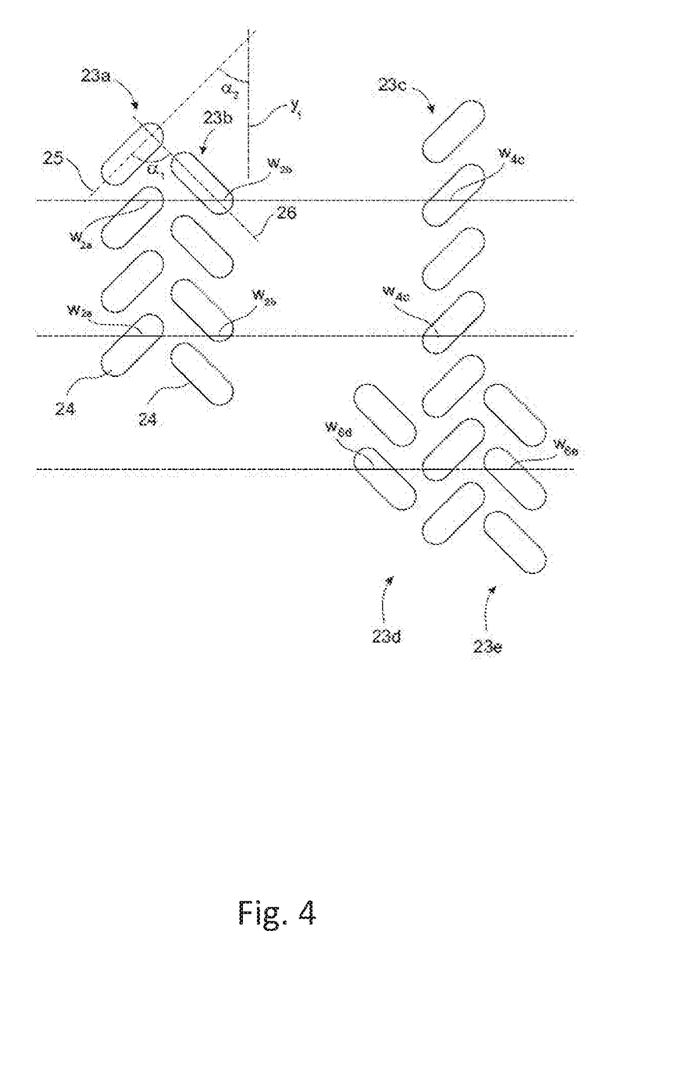
FIG. 4 shows a further partial view of a welding pattern and welding spots.
Figure 5:
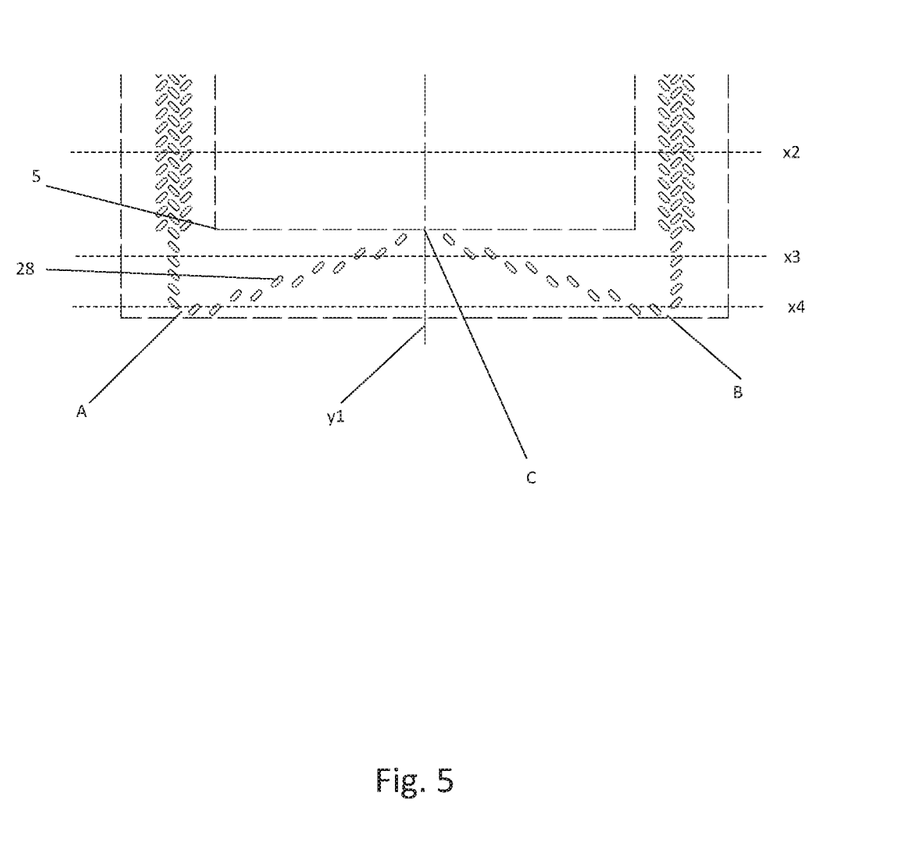
FIG. 5 shows a view of a connecting sealing.

With reference to FIGS. 3, 4 and 5, the sealing arrangement 15, 16, 27, 28 may be constituted by a welding pattern 23 produced by means of a thermo and/or mechanical sealing, such as ultrasonic welding or thermo-sealing. The welding pattern 23 may comprise welding spots 24 which are arranged in different formations forming the sealing arrangement 15, 16, 27, 28. A part of the welding pattern 23 may be arranged in the form of a first longitudinal row 23a in which the welding spots 24 are arranged along a first axis 25. Also, a further number of welding spots 24 are arranged in the form of a second longitudinal row 23b in which the welding spots 24 extend along a second axis 26. Furthermore, the first axis 25 and the second axis 26 extend in a manner so that they define a first angle α1 in relation to each other. In this manner, it can be ensured that the absorbent core 5 can be manufactured with a high level of sealing strength in both its longitudinal and transversal direction. The strength provided by means of a welding process for producing the sealing arrangement 15, 16, 27, 28 may be optimized by using the above-mentioned configuration of the welding pattern 23. The sum of the area of the welding spots 24 is constant along the direction of the transversal axis x1. As disclosed in FIG. 1, the transversal axis x1 extends along the width of the absorbent article 1, the sum of the area of the welding spots 24 is constant along this direction. As shown in FIG. 1, there are six welding spots 24 on each row along the direction of the transversal axis $x1$, hence the sum of the area of the welding spots 24 along the direction of the transversal axis $x1$ in FIG. 1 is the sum of the area of each of the six welding spots 24 on a row in the transversal direction. FIG. 5 discloses three transversal axis on three different rows $x2$, $x3$, $x4$, each axis crossing through six welding spots 24. Thus, the sum of the area of the welding spots 24 in each transversal axis $x2$, $x3$, $x4$ are all equal to each other. During the manufacturing process, the welding spots 24 may be welded with constant energy transfer in the direction of the longitudinal axis $y1$ of the absorbent article 1 and the sum of the welding spots 24 may obtain a constant area along each transversal row. As disclosed in FIG. 1, the absorbent article 1 may have two connecting sealings 27, 28 wherein the connecting sealings 27, 28 do not extend beyond the length of the side seams 15, 16 in the longitudinal direction.

The area of each individual welding spot along a row in the transversal direction of the absorbent article may vary. The number of welding spots 24 in the transversal direction may also vary. Thus, the individual welding spots 24 in a first transversal row may have a first area and the individual welding spots 24 in a second transversal row may have a second area, yet the sum of the area of the welding spots 24 in the transversal direction is equal for each row.

During the manufacturing process the welding spots 24 may be welded such that the sum of the area of the welding spots 24 is constant along the direction of the transversal axis and such that the sum of the amount of welding spots 24 along the direction of the transversal axis $x1$ is constant. In other words, the area and the sum of the welding spots 24 along the transversal direction may be constant. The sum of the welding spots 24 along the transversal direction may be within the range of 2-20, such as within the range of 4-8.

As disclosed in FIG. 1 and FIG. 5, the welding spots 24 can be configured in different arrangements. The minimum distance between each adjacent welding spot of the sealing arrangement 15, 16, 27, 28 may vary. The minimum distance between each adjacent welding spot in the first connecting sealing 27 may be greater or smaller than the minimum distance between each adjacent welding spot in the second connecting sealing 28. Further, the minimum distance between each adjacent welding spot in the connecting sealings 27, 28 may be greater than or less than the minimum distance between each adjacent welding spot in the side seams 15, 16 or the channel sealings 9, 10. As disclosed in FIG. 5, the welding spots 24 may be arranged in pair of two, the minimum distance between each individual welding spot in a pair of welding spots 24 may then be smaller than the minimum distance between two adjacent pair of welding spots 24. The possibility to vary the distance between the welding spots 24 in the sealing arrangement 15, 16, 27, 28 allows for configuring the welding spots 24 in different welding patterns 23. This allows for changing the form and/or structure of the sealing arrangement 15, 16, 27, 28 to optimize the absorbent article construction. Some configurations may be more beneficial for the absorbent article 1 fit and some configurations may be more beneficial for the rigidness of the absorbent article 1. Further, the welding pattern 23 may be modified to fit or to generally follow the form of other elements of an absorbent article, such elements may be the outline of the absorbent component 5a, 5b, 5c or the absorbent core 5, etc. The term "minimum distance" refers to the minimal distance from the edge of one welding spot to the closest edge of an adjacent welding spot. This distance may be within the range of 0.001 mm to 40 mm.

As disclosed in FIG. 1 and FIG. 5 the at least one connecting sealings 27, 28 may comprise a first point A, being adjacent to one side seam 15, a second point B being adjacent to the other side seam 16 and a third point C located along the longitudinal axis $y1$. The three points A, B, C may form a triangular shape. The points A to B may form a first line that has a first length extending along the direction of the transversal axis $x1$ creating the base of the triangle and the point C creating the apex. Further, the point C may form a second line having a second length, extending from C to the base of the triangle following the longitudinal axis $y1$. In other words, the first and second connecting sealings 27, 28 may have three points A, B and C forming a triangular shape, the point C defining the apex, and the points A to B forming the base, wherein the distance in longitudinal direction between the apex of the triangle to the base of the triangle may vary. The distance from the apex to the base of the triangle may also be called "the maximum length" of the at least one connecting sealing 27, 28. The maximum length of a first connecting sealing 27 and a second connecting 28 sealing may differ. The maximum length in longitudinal direction of the first connecting sealing 27 may be greater than the maximum length in longitudinal direction of the second connecting sealing 28.

The connecting sealings 27, 28 may generally have a V-shape or an arrow shape, where the tip of the V or the arrow may be the point C. The V-shaped or Arrow shaped at least one connecting sealing 27, 28 may point inwardly towards the transversal axis $x1$ and/or point outwardly away from the transversal axis $x1$. Such a shape of the at least one connecting sealing 27, 28 allows for a more efficient manufacturing process. Since the manufacturing is with constant energy transfer there could arise challenges to form the connecting sealings 27, 28 and side seams 15, 16 with a constant energy process, hence the V-shape is a solution that allows the sealing arrangement 15, 16, 27, 28 to be produced in such a manner. Further, it may result in improved core integrity. The sealing arrangement 15, 16, 27, 28 may have a first and a second connecting sealing 27, 28, wherein the first and second connecting sealings 27, 28 are V-shaped pointing towards each other.

As disclosed above, the points in the at least one connecting sealing 27, 28 may form a triangle and the height of the triangle is named the "second length" as well as the "maximum length"

As shown in FIG. 1 and FIG. 5 the second length of the first connecting sealing 27 and the second connecting sealing 28 may vary. The shorter the second length is, the greater the minimum distance between the adjacent welding spots 24 and/or adjacent welding spot pairs may be. An absorbent article 1 may be configured to have less of the absorbent component 15a, 15b, 15c in the front portion 6, which may result in that the second length may be greater for the first connecting sealing 27. Further, the second length of the at least one connecting sealings 27, 28 could be varied to achieve less minimum distance between the welding spots 24 and/or pair of welding spots 24 in respective connecting sealing 27, 28. A smaller minimum distance could improve the rigidness of the welding since there is a smaller length between the welding spots 24 or the pair of welding spots 24. In FIG. 1, the second length of the connecting sealing 27 in the front portion 6 is greater than the second length of the connecting sealing 28 in the back portion 7.

As disclosed in FIG. 1, the at least one connecting sealing 27, 28 may be symmetrically aligned with respect to the longitudinal axis $y1$.

Further, the first connecting sealing 27 may form an angle with respect to the longitudinal axis y1. This angle may be equal to or less than 90 degrees. The second connecting sealing 28 may also form an angle with the longitudinal axis y1, this angle may be equal to or more than 90 degrees, which is disclosed in FIG. 1 where the first connecting sealing 27 form an angle of less than 90 degrees and the second connecting sealing 28 forms an angle of more than 90 degrees. The angle may be measured by connecting the welding spots 24 in the connecting sealings 27, 28 with a straight line and further measuring the angle between the line and the longitudinal axis y1 at the point C.

Each welding spot has a length and a width and the length may be at least 1.1 or 1.2 times greater than the width. The length of each welding spot may be 1-6 mm, or 1.5-4.5 mm. The width of each welding spot may be 0.5-3.0 mm or 0.8-1.2 mm. The welding spots 24 may be of generally circular, rectangular, oval or oblong shape. The distance between two adjacent welding spots 24 in the longitudinal direction of the article may be 1-5 mm, measured from the centre point of each welding spot.

The above-mentioned first angle α1 may be in the interval of 45-130°, 45-100°, or 45-70°. As shown in FIGS. 3 and 4, the first angle α1 may be in the magnitude of 90°.

Also, as shown in FIGS. 3 and 4, the first axis 25 may define an angle α2 with reference to said longitudinal axis y1 which may be within the interval 30-60°.

FIG. 4 teaches one row 23c of welding spots 24 in each side seam 15, 16 along the crotch portion 8, and three rows 23c, 23d, 23e of welding spots 24 in each side seam 15, 16 along the front portion 6 and the back portion 7, respectively. Also, each side seam 15, 16 may define a fifth side seam width w5 and a sixth side seam width w6 along the front portion 6 and back portion 7, respectively.

By using an ultrasonic welding pattern 23 as mentioned above, there is provided an absorbent article 1 with high sealing strength in both its longitudinal and transversal direction. In this manner, high demands during wear and handling of such an absorbent article 1 may be fulfilled.

As shown in FIGS. 3 and 4, the width w2 of the first row 23a and the second row 23b may be defined as an "effective" width in the sense that it is equal to the sum of an effective width w2a of a welding spot 24 in the first row 23a and an effective width w2b of a welding spot 24 in the second row 23b. Each "effective width" can be defined as the length of a welding spot 24 in a transverse direction of the article 1, as indicated in FIG. 4. Similarly, the effective width w4c and w6c, respectively, of the third row 23c of welding spots 24 is also shown in FIG. 4. The effective width of the third row 23c in the crotch portion 8 is the length w4c of a welding spot 24 in said transverse direction, as indicated in FIG. 4. Also, the effective width of the side seam 16 outside the crotch portion 8 (as also indicated in FIG. 1) i.e., the combined effective width of the three rows 23c, 23d, 23e forming the side seam 16 is the sum of the lengths w6c, w6d, w6e in said transverse direction, as shown in FIG. 4.

The sum of the effective widths in a transversal direction of the article 1 may be generally constant along the longitudinal length of the core 5. This is advantageous in a manufacturing process involving ultrasonic welding of the connecting sealings 27, 28 channels sealings 9, 10 and the side seams 15, 16, since the manufacturing process can be arranged so that a generally constant energy transfer is required as the ultrasonic welding of the channels sealings 9, 10 and side seams 15, 16 is produced along the longitudinal direction of the core 5.

There is also provided a method for manufacturing an absorbent article 1 comprising a longitudinal axis y1 and a transversal axis x1 extending in a perpendicular direction in relation to the longitudinal axis y1 and said article comprising a front portion 6, a back portion 7 and a crotch portion 8. The method may comprise the steps of:
- forming an absorbent core 5 with an absorbent component 5a, 5b, 5c and enclosing said absorbent component 5a, 5b, 5c in a core cover comprising an upper side 11 and a lower side 12;
- providing two side seams 15, 16 and at least one connecting sealing 27, 28 joining said upper 11 and lower sides 12; and
- sandwiching said absorbent core 5 between a liquid-permeable topsheet 3 and a liquid-impermeable backsheet 4.

Furthermore, the method comprises, forming said two side seams 15, 16 and at least one connecting sealing 27, 28 by a thermo and/or mechanical welding process comprising a plurality of welding spots 24 being welded along the direction of the longitudinal axis y1, wherein the sum of the area of the welding spots 24 is constant along the direction of the transversal axis x1.

The absorbent core 5 is formed by an absorbent component 5a, 5b, 5c which defines the core 5 by enclosing said absorbent component 5a, 5b, 5c between the upper core cover side 11 and the lower core cover side 12. Next, the side seams 15, 16 are formed in a manner so that they join the upper side 11 and the lower side 12. The sealings may be formed by ultrasonic welding.

Consequently, the absorbent core 5 may be formed with an absorbent component 5a, 5b, 5c enclosed by a core cover 11, 12 and the sealing arrangement 9, 10, 15, 16 comprising the at least one connecting sealing 27, 28 and the side seams 15, 16. The upper core cover side 11 and the lower core cover side 12 are joined to define said sealing arrangement 15, 16, 27, 28.

The article 1 (see FIG. 1) is formed by sandwiching the absorbent core 5 between the liquid-permeable topsheet 3 and the liquid-impermeable backsheet 4. The article 1 defines the longitudinal axis y1 and the transversal axis x1 as described above. Also, the article 1 defines a front portion 6, a back portion 7 and a crotch portion 8

The absorbent component 5 may be formed so that the total amount of absorbent material of the centre segment 5a is generally equal to, or greater than, the total amount of absorbent material in each one of the side segments 5b, 5c. Furthermore, the manufacture method may be configured so that the absorbent core 5 is formed so that that the ratio of the first width a1 and the third width b1 is greater than the ratio of the second width a2 and the fourth width b2. This corresponds to the description above with reference to FIGS. 1 and 2.

The at least one connecting sealing 27, 28 and the side seams 15, 16 may be welded such that a welding apparatus travels along the absorbent article following the longitudinal axis y1 starting from the front or back portion 6, 7 of the absorbent article 1 and performing the welding process during its travel throughout the whole length of the absorbent article 1. The disclosure may be varied within the scope of the appended claims. For example, the materials and dimensions used for the different layers forming the absorbent article 1 may be varied, as indicated above. The absorbent article may further include leg elastics, standing gathers, crotch and waist elastics, side panels, fastening systems, etc., as known to the skilled man in the art and depending of the type of absorbent article intended.

The invention claimed is:

1. An absorbent article comprising an absorbent core sandwiched between a liquid-permeable topsheet and a liquid-impermeable backsheet, said article being arranged along a longitudinal axis and a transversal axis extending in a perpendicular direction in relation to the longitudinal axis and said article defining a front portion, a back portion and a crotch portion,
   wherein said absorbent core comprises an absorbent component enclosed by a core cover comprising an upper side and a lower side, and welding spots for joining said upper and lower sides,
   wherein said welding spots comprise two side seams extending along two side edges in the direction of the longitudinal axis of said core,
   wherein said welding spots further comprise at least one transversally oriented connecting sealing, said at least one connecting sealing joining said side seams, and
   wherein a sum of an area of the welding spots is constant along the direction of the transversal axis.

2. The absorbent article according to claim 1, wherein the welding spots further comprise two channel sealings extending along said longitudinal axis in said crotch portion.

3. The absorbent article according to claim 1, wherein the absorbent component does not extend beyond the welding spots.

4. The absorbent article according to claim 1, wherein the absorbent article comprises a first connecting sealing and a second connecting sealing, wherein said first connecting sealing joins said side seams at the front portion and wherein said second connecting sealing joins said side seams at the back portion of the absorbent core.

5. The absorbent article according to claim 1, wherein a sum of a number of welding spots along the direction of the transversal axis is constant.

6. The absorbent article according to claim 4, wherein the at least one connecting sealing is symmetrically aligned with respect to the longitudinal axis.

7. The absorbent article according to claim 6, wherein:
   the angle, facing a front-most portion of the absorbent article, between the longitudinal axis and the first connecting sealing, is less than 90 degrees; and
   the angle, facing the front-most portion of the absorbent article, between the longitudinal axis and the second connecting sealing, is more than 90 degrees.

8. The absorbent article according to claim 4, wherein the welding spots include first welding spots in the first connecting sealing and second welding spots in the second connecting sealing, wherein a minimum distance between the first welding spots in the transversal direction in the first connecting sealing differs from a minimum distance between the second welding spots in the second connecting sealing.

9. The absorbent article according to claim 1, wherein the welding spots generally follow the outline of the absorbent component in at least one part of the welding spots.

10. The absorbent article according to claim 1, wherein at least one connecting sealing generally follows the outline of the absorbent component, wherein at least one connecting sealing deviates from the shape of the absorbent component.

11. The absorbent article according to claim 4, wherein the maximum length in the longitudinal direction of the first connecting sealing differs from the maximum length in longitudinal direction of the second connecting sealing.

12. The absorbent article according to claim 11, wherein the maximum length in the longitudinal direction of the first connecting sealing is greater than the maximum length in the longitudinal direction of the second connecting sealing.

13. The absorbent article according to claim 1, wherein at least one connecting sealing is generally V-shaped.

14. The absorbent article according to claim 1, wherein the welding spots are circular, rectangular, oblong or oval shaped.

15. The absorbent article according to claim 1, wherein a sum of a number of welding spots along the transversal direction is within the range of 2-20.

* * * * *